United States Patent [19]

Moore et al.

[11] Patent Number: 4,555,176

[45] Date of Patent: Nov. 26, 1985

[54] METHOD AND APPARATUS FOR DETERMINING PRESSURE-INDUCED FREQUENCY-SHIFTS IN SHOCK-COMPRESSED MATERIALS

[75] Inventors: David S. Moore; Stephen C. Schmidt, both of Los Alamos, N. Mex.

[73] Assignee: The United States of America as represented by the United States Department of Energy, Washington, D.C.

[21] Appl. No.: 562,150

[22] Filed: Dec. 16, 1983

[51] Int. Cl.[4] .......................................... G01N 21/65
[52] U.S. Cl. ................................................... 356/301
[58] Field of Search ........................................ 356/301

[56] References Cited

U.S. PATENT DOCUMENTS 4,398,801  8/1983  McWilliams ........................ 350/275

OTHER PUBLICATIONS

"Stimulated Brillouin Scattering in Shock-Compressed Fluids," Bloom et al., *J. App. Phys.*, vol. 45, No. 3, Mar. 1974 p. 1200.
"Backward Stimulated Raman Scattering in Shock Compressed Benzene," Schmidt et al., *Phys. Rev. Lett.*, vol. 50, No. 9, Feb. 28, 1983, p. 661.
"Simultaneous Multimode Pressure-Induced Frequency-Shift Measurements in Shock Compressed Organic Liquid Mixtures by Use of Reflected Broadband Coherent Anti-Stokes Raman Scattering," Moore et al., *Phys. Rev. Lett.*, vol. 50, No. 22, May 30, 1983, p. 1819.
"Coherent Raman Spectroscopy," Levenson, *Physics Today*, May 1977, pp. 44-49.
"Dynamic Compression of Liquids From Measurements on Strong Shock Waves," Walsh et al., *J. Chem. Phys.*, vol. 26, No. 4, Apr. 1937, p. 815.
"Stimulated Brillouin Scattering in Shock Compressed Fluids," Keeter et al., *Phys. Rev. Lett.*, vol. 17, No. 16, Oct. 17, 1966, p. 852.
"Stimulated Brillouin Scattering in Liquids," Brewer et al., *Phys. Rev. Lett.*, vol. 13, No. 11, Sep. 14, 1964, p. 334.
Los Alamos Unclassified Report 83-1024, Moore et al., Proceedings of the Los Alamos Conference on Optics '83, released 4/7/83.
Los Alamos Unclassified Report 83-351, Schmidt et al., presented at Ninth International Colloquium on Dynamics of Explosions and Reactive Systems, Poitier, France, Jul. 4-8, 1983.
Los Alamos Unclassified Report 83-901, Schmidt et al., presented at Workshop on Shock-Compressed Chemistry in Materials Synthesis and Processing, Seattle, WA. Mar. 28-29, 1983.
Los Alamos Unclassified Report 83-1584, Schmidt et al., presented at Conference on Shock-Waves in Condensed Matter, Santa Fe, NM, Jul. 18-21, 1983.
Los Alamos Unclassified Report 83-1854, Moore et al., presented at IX AIRADT Conference, Albany, NY, Jul. 25-29, 1983.
Los Alamos Unclassified Report 83-2847, Schmidt et al., presented at CEA/Los Alamos High Explosives and Detonation Physics Conference, Paris, France, Oct. 3-6, 1983.

*Primary Examiner*—F. L. Evans
*Assistant Examiner*—Joel L. Harringa
*Attorney, Agent, or Firm*—William A. Eklund; Paul D. Gaetjens; Judson R. Hightower

[57] ABSTRACT

A method and an apparatus for conducting coherent anti-Stokes Raman scattering spectroscopy in shock-compressed materials are disclosed. The apparatus includes a sample vessel having an optically transparent wall and an opposing optically reflective wall. Two coherent laser beams, a pump beam and a broadband Stokes beam, are directed through the window and focused on a portion of the sample. In the preferred embodiment, a projectile is fired from a high-pressure gas gun to impact the outside of the reflective wall, generating a planar shock wave which travels through the sample toward the window. The pump and Stokes beams result in the emission from the shock-compressed sample of a coherent anti-Stokes beam, which is emitted toward the approaching reflective wall of the vessel and reflected back through the window. The anti-Stokes beam is folded into a spectrometer for frequency analysis. The results of such analysis are useful for determining chemical and physical phenomena which occur during the shock-compression of the sample.

12 Claims, 3 Drawing Figures

METHOD AND APPARATUS FOR DETERMINING PRESSURE-INDUCED FREQUENCY-SHIFTS IN SHOCK-COMPRESSED MATERIALS

This invention is the result of a contract with the Department of Energy (Contract No. W-7405-ENG-36).

BACKGROUND OF THE INVENTION

This invention is generally related to methods and apparatus for the spectroscopic analysis of shock-compressed materials. More specifically, the present invention is related to the analysis of shock-compressed transparent liquids and solids by the use of coherent anti-Stokes Raman scattering (CARS) spectoscopy.

A continuing project of the Los Alamos National Laboratory is the study of the chemical and physical characteristics of materials at temperatures and pressures approaching those which exist in detonations of high explosives. Such characteristics are useful for determining equations of state for such materials and for predicting the behavior of explosives in various environments and configurations.

For many purposes, it is sufficient and useful to determine the physical and chemical characteristics of materials which are shock-compressed to high temperatures and pressures by mechanical means rather than by the use of explosives, thus enabling simpler and safer experiments to be conducted under controlled conditions which to some extent simulate the conditions in an explosive detonation. The present invention is directed to a novel spectroscopic technique which is particularly useful for observing and determining vibrational frequencies of shock-compressed organic liquids.

Light impinging on a molecule is ordinarily partially scattered by an elastic scattering process known as Rayleigh scattering. However, a small fraction of the light may undergo inelastic, or Raman, scattering. In Raman scattering a portion of the energy of the impinging photon is absorbed by the molecule, resulting in the scattered photon having a lower energy (and longer wavelength) than that of the impinging photon. In both of these processes, the molecule is excited by the impinging photon to a virtual energy level. In Rayleigh scattering the molecule decays back to the initial energy level, whereas in Raman scattering the molecule decays to an excited vibrational level which is typically the $v=1$ vibrational state. The difference in energy between the impinging photon and the emitted Raman photon is equal to the energy difference between the ground and $v=1$ vibrational states.

In the technique known as coherent anti-Stokes Raman spectroscopy, two laser beams are utilized. One laser beam is used to excite the molecule to the virtual energy level and the other beam is used to stimulate decay of the molecule from the virtual energy level to the excited vibrational state, resulting in Raman emission from the excited molecule. The first laser beam is referred to as the pump beam and the second beam is referred to as the Stokes beam. The function of the Stokes beam is to stimulate Raman emission from the population of molecules in the excited virtual energy state and thereby create a coherent population of molecules in the excited vibrational state. This population of molecules in the excited vibrational level is then susceptible to further coherent excitation by the pump beam, which excites them to a second virtual energy level that is higher than the virtual energy level which was attained by pumping of the molecule from the ground state. The molecules that are excited to the second, higher virtual energy level can then decay to the ground energy state. This latter decay occurs by coherent emission, resulting in a laser beam (known as the anti-Stokes beam) which has an energy (and frequency) that is higher than that of either the pump beam of the Stokes beam. This sequence of events actually occurs simultaneously through a four-wave mixing process. From the observed frequency of the anti-Stokes beam, the energy level of the $v=1$ vibrational state can be determined from the relationship $\omega_r = \omega_{as} - \omega_p$, where $\omega_r$ is the frequency for the transition from the ground vibrational state to the $v=1$ vibrational level, $\omega_p$ is the frequency of the pump beam, and $\omega_{as}$ is the frequency of the anti-Stokes beam. This technique is generally known as coherent anti-Stokes Raman spectroscopy (CARS).

As discussed further below, the present invention is essentially an application of a variation of the above-described technique, which is known as broadband coherent anti-Stokes Raman scattering spectroscopy (broadband CARS), to shock-compressed condensed-phase materials. The applicants and others have recently applied a related technique known as backward-stimulated Raman scattering (BSRS) to vibrational frequency shifts in shock-compressed liquids. However, the latter technique suffers from a relative disadvantage in that only the Raman-active vibrational mode with the largest transition cross section undergoes stimulated scattering. This precludes detection of more than one chemical species or more than one vibrational mode in a single species. In addition, for some molecules the incident power density required to induce scattering is large enough to damage optical components located near focal points.

SUMMARY OF THE INVENTION

Accordingly, the object of the present invention is to provide an improved method and apparatus for applying the technique of coherent anti-Stokes Raman scattering spectroscopy to shock-compressed liquids.

It is also an object of the present invention to provide a method and apparatus for applying coherent anti-Stokes Raman scattering spectroscopy to shock-compressed liquids such that more than one molecular species can be detected and such that more than one vibrational mode of a single species can be detected.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention as embodied and broadly described herein, the present invention is a method which is referred to herein as reflected broadband coherent anti-Stokes Raman scattering spectroscopy (RBBCARS). In accordance with this method, a liquid or transparent solid sample is shock-compressed by means of an optically reflective compression element which may be driven by any suitable means. In the preferred embodiment of the apparatus of the invention, which is described further below, the compression element is a polished, optically reflective stainless steel plate that forms one wall of a containment vessel for the sample to be analyzed. The steel plate is destructively driven by a projectile fired from a high-pressure gas gun. Two laser beams are directed into the shock-compressed sample toward the reflective plate at the moment of shock-compression of the sample. The two laser beams intersect at a small angle at a focal point within the sample, resulting in the emission of a coherent anti-Stokes beam, which is reflected by the moving stainless steel plate and folded into a spectrometer for analysis.

BRIEF DESCRIPTION OF THE DRAWINGS

The accompanying drawings, which are incorporated in and form a part of the specification, illustrate a preferred embodiment of the apparatus of the present invention and, together with the description, serve to explain the principles of the invention. In the drawings.

DETAILED DESCRIPTION OF THE INVENTION

Figure 1:
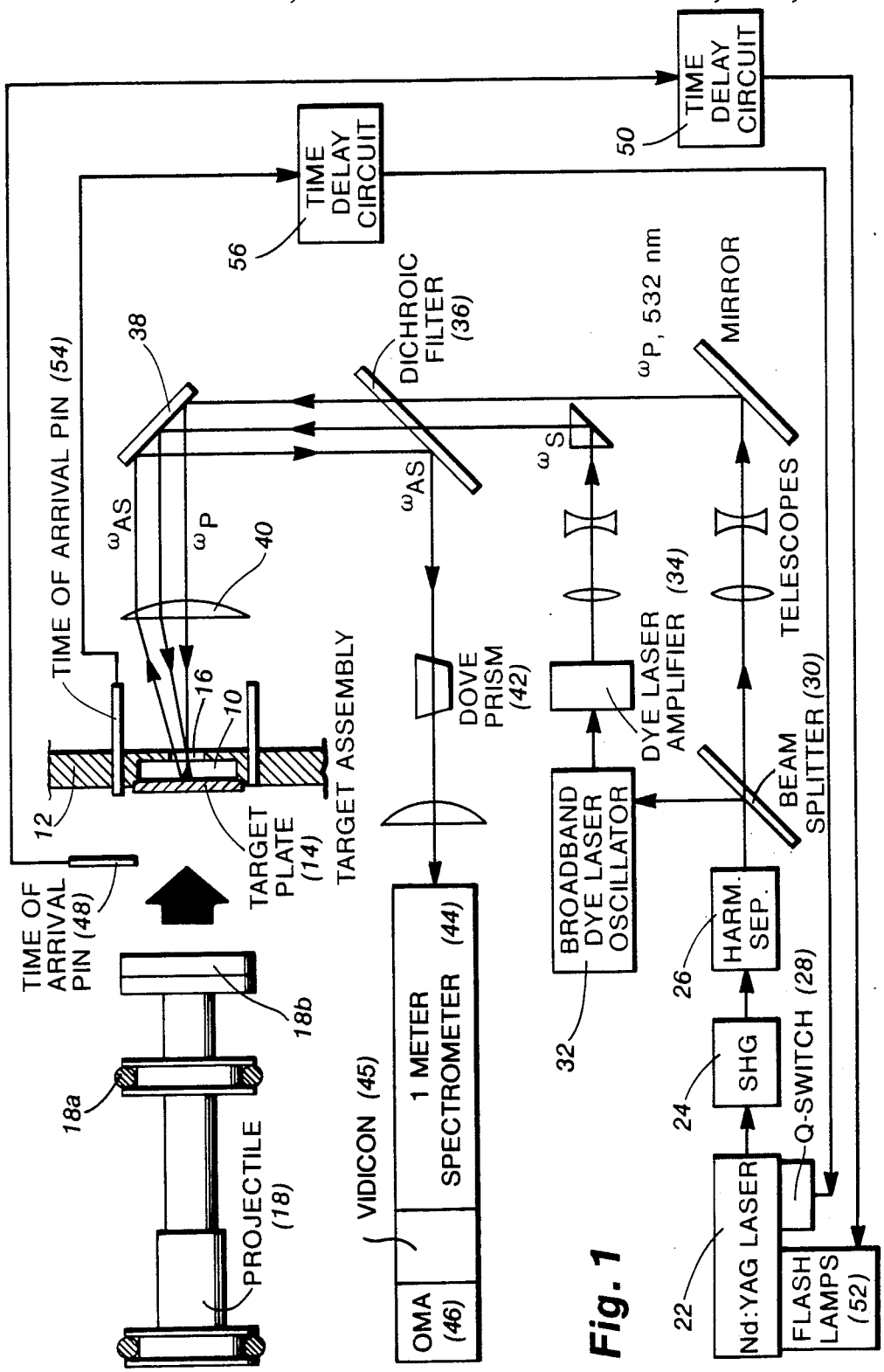
FIG. 1 is a schematic diagram of the apparatus.
Figure 2:
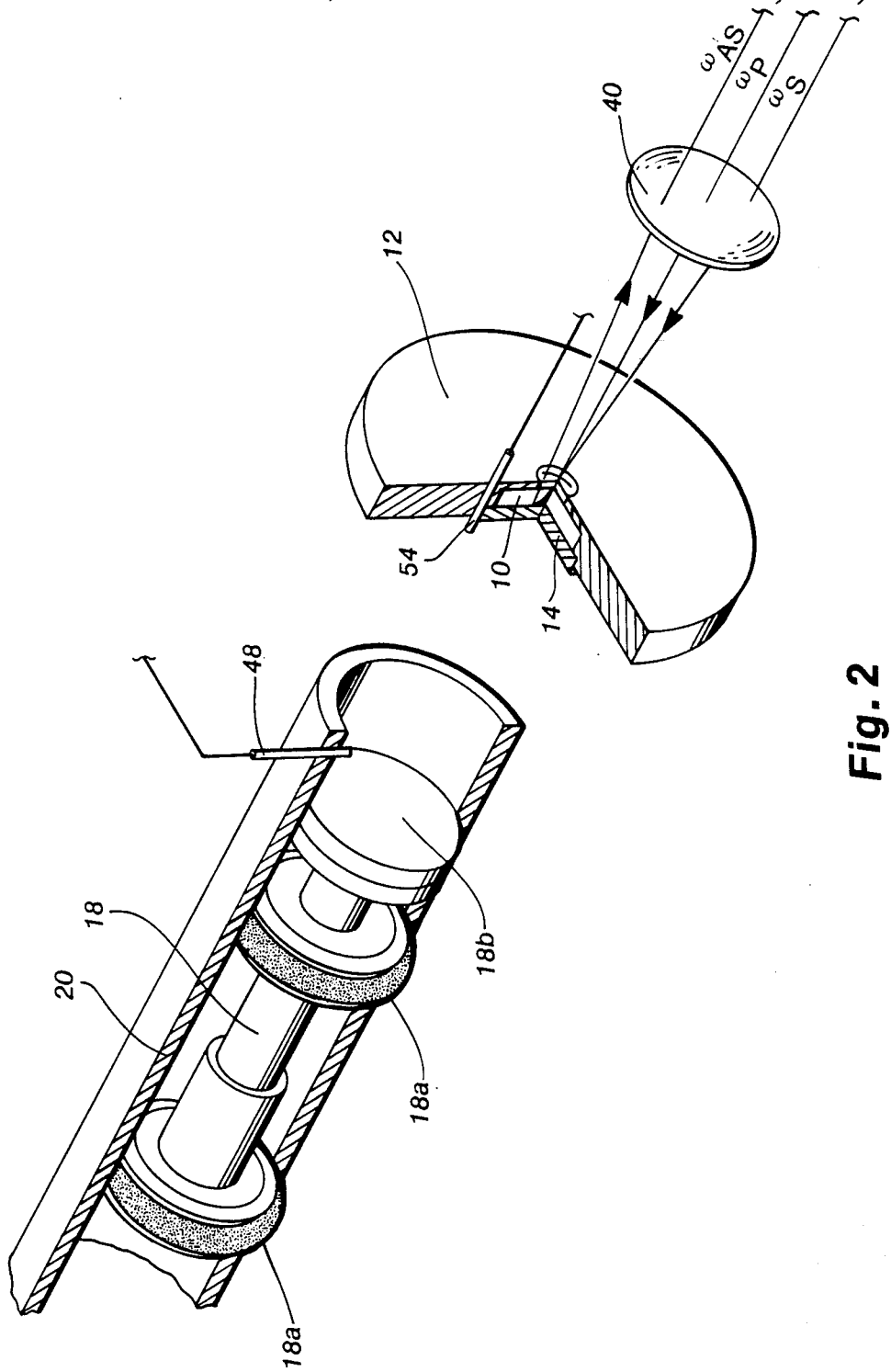
FIG. 2 is a partially exploded pictorial view of the gas gun barrel, projectile and sample plate assembly of the present invention.

Referring to FIGS. 1 and 2, a sample of a transparent organic liquid is contained in a cylindrical cavity 10 which is formed in the center of a circular one-half inch thick aluminum sample plate 12. The liquid is contained on one side by means of a 2.1 mm thick stainless steel target plate 14 and on the other side by means of a small circular glass window 16. The cavity 10 is approximately 8 mm thick between the target plate 14 and the window 16, and is approximately 38 mm in diameter. The target plate 14 is polished to a mirror finish on its inside surface. Stainless steel is preferred in the construction of the target plate because experience has shown that it retains its optical reflectivity under shock-compression conditions.

The liquid in the sample cavity is shock-compressed by means of an approximately 300 gm magnesium projectile 18 which is propelled by compressed helium along the barrel 20 of a 3.3 meter-long, 51 mm-diameter air gun. Prior to firing, the sample plate 12 is sealed flush against the muzzle of the gun barrel 20 and the bore of the barrel is evacuated. The projectile includes two O-ring gas seals 18a and a stainless steel head 18b bonded to the magnesium body of the projectile. The projectile 18, the sample plate 12 and the optical components in front of sample plate are destroyed with each firing. In a typical run the projectile 18 is accelerated to a velocity of approximately 0.7 km/sec at the point of impact, generating a shock-compression pressure in the liquid sample of approximately 10 to 15 kilobars (kBar). Upon the impact of the projectile against the target plate, a substantially planar shock wave travels forwardly through the liquid sample at a speed several times greater than the speed at which the target plate is driven. Behind the shock wave there is produced a shock-compressed zone within the liquid sample, which is analyzed in the manner described below.

Two laser beams, which are referred to herein as the pump beam and the Stokes beam, are directed into the sample cavity 10 so as to intersect at a focal point in the liquid sample. These beams are designated $\omega_p$ and $\omega_s$, respectively, in FIG. 1. The pump beam is generated by a pulsed neodymium-doped yttrium aluminum garnet (Nd:YAG) laser 22. The pump beam is of medium energy (1–5 millijoules) and is frequency-doubled by means of a second harmonic generator (SHG) 24 and a harmonic separator 26 so as to have a frequency of 532 namometers (nm) and energy of 1–5 millijoules. A single 6 nanosecond pulse is used. The timing of the firing of the Nd:YAG laser is controlled by an electro-optic Q switch 28 which is triggered by the arrival of the projectile at the sample, as further described below.

A portion of the pump beam is split off by a beam spliter 30 and is used to generate the Stokes beam by means of a dye laser oscillator 32 (Rhodamine 590 dye) and associated dye laser amplifier 34, which produce a broadband Stokes beam having a frequency range of approximately 580 to 600 nm. The pump beam and Stokes beam are transmitted along parallel paths through a long-wavelength-pass dichroic filter 36 and are folded into the sample cavity by means of disposable mirror 38 and lens 40 which are mounted in front of the cavity. The beams are focused and crossed within the sample cavity, with an overlap length of approximately 1 mm. The focal point is approximately 4 mm in front of the polished surface of the target plate. The beam crossing angle is adjusted by adjusting the axial distance between the two parallel beams, using a precision translation stage on the dye laser turning prism.

The interaction of the pump and Stokes beams with the sample liquid results in the generation of a CARS beam (denoted $\omega_{as}$ in FIG. 1), which is emitted generally in the direction toward the reflective surface of the target plate 14. The CARS beam is reflected by the target plate and passed out of the sample through the window 16 along a path generally parallel to the two incoming beams $\omega_p$ and $\omega_s$. The CARS beam $\omega_{as}$ is separated from the pump and Stokes beams with the long-wavelength-pass dichroic filter 36 and then passed through a dove prism 42 and focused onto the 75 micrometer-wide entrance slit of a 1-meter spectrometer 44. The purpose of the dove prism 42 is to rotate the image of the CARS beam by 90° so that any beam movement resulting from the movement of the target plate is translated to movement along, rather than across, the spectrometer entrance slit. The spectrometer includes a 1200 line/mm grating which is blazed at 500 nm and used in first order. The spectrometer is calibrated using known atomic emission spectra from a mercury vapor lamp. The signals from the spectrometer 44 are detected at the exit of the spectrometer with a silicon-intensified-target vidicon 45 (EGG-PAR 1205D) coupled to an optical multi-channel analyzer (OMA) 46 (EGG-PAR 1205A).

Timing of the laser pulses to coincide with the shock compression of the liquid sample is achieved with time-of-arrival pins which are mounted in the sample plate and in the bore of the gas gun. A first pin 48 is mounted in the barrel of the gun approximately 25 cm up the bore from the target assembly. Upon being passed by the projectile the pin 48 produces a timing signal which is transmitted to a time delay circuit 50. The time delay circuit 50 produces a delayed timing signal after a delay of approximately 300 microseconds. The delayed timing signal actuates the flash lamps 52 of the Nd:YAG laser, initiating optical charging of the laser rods. A second time-of-arrival pin 54 is located immediately behind the target plate. Upon being struck by the projectile, the second pin 54 produces a second timing signal, which is delayed by a second time delay circuit 56. The delayed signal from the second time delay circuit is applied to the Q-switch 28 in the Nd:YAG laser.

One characteristic of the anti-Stokes CARS output beam is that it is emitted in nearly the same direction as that of the incoming pump and Stokes beams. This occurs as a consequence of what is known as phase matching, which is essentially a conservation-of-momentum requirement that is applicable in coherent laser phenomena. The emission of the CARS beam in the same direction as the input beams, i.e., away from the window of the target chamber, necessitates the use of the reflective target plate, and also results in certain advantages which are discussed below.

The phase matching requirement described above results in input and output beams which are exactly collinear when the index of refraction is the same for the two input beams and the output beam. However, there is ordinarily some variation in the index of refraction with frequency (i.e., some dispersion), and as a result true collinear phase matching is not obtained. Also, the input pump and Stokes beams are not exactly parallel, since they are deliberately focused so as to intersect at a small angle over a small volume (approximately 0.5 mm long by 15 micrometers wide) of the shock-compressed liquid. As a result, the CARS beam is emitted at a small angle with respect to both the pump and Stokes beams; however, this angle is sufficiently small that the CARS beam nevertheless is reflected by the polished surface of the target plate and is returned through the window 16 of the sample chamber.

One factor that must be considered in focusing the input beams on a common focal point within the sample liquid is that the index of refraction of the liquid changes as it is shock-compressed. Since the frequencies of the two beams are not identical and the index of refraction is frequency- as well as pressure-dependent, it is not always possible to exactly predict the focal points of the two beams. This problem is largely avoided, however, by introducing both beams into the chamber at a small angle to one another, so that they overlap over some distance, thereby accommodating small uncertainties in the actual focal points. In addition, the use of non-Gaussian cross-section laser beams leads to relaxed phase-matching angle tolerances. This effect allows sufficient phase-matching for CARS beam generation in the shock-compressed sample when the signal generation and detection are optimized using an ambient sample.

It will be recognized that there is a fundamental advantage obtained in introducing the two input laser beams, and returning the resulting anti-Stokes CARS beam, along a common axis which is essentially parallel to the direction of travel of the shock wave. This advantage lies in the fact that there is avoided most of the refraction and dispersion of the laser beams that would otherwise ordinarily result from the rarefaction waves that are generated in the shock-compressed liquid. Such waves are ordinarily generated at the traveling interface between the nearly-planar shock wave and the cylindrical walls of the sample chamber. These rarefaction waves travel radially inwardly from the chamber walls toward the center of the chamber. By using a sample chamber that is relatively short in the axial direction and relatively large in diameter, and by directing the laser beams along the axis of the shock wave as just noted, measurements can be obtained from the central portion of the shock-compressed liquid before that portion is disturbed by incoming rarefaction waves. Moreover, this measurement is obtained without any of the three laser beams having to pass through any rarefaction waves. This is to be contrasted, for example, with a simple but inferior alternative approach to the present invention, which would be to direct the input laser beams through a window in one side of a shock wave tube and to collect the output CARS beam through a window on the opposite side of such a tube, such that both the input and output beams would be transverse to the direction of travel of the shock wave. With such an arrangment the need for the reflective target plate would be avoided, but at the same time there would be introduced substantial distortion of both the input and output beams as a result of rarefaction waves generated behind the shock wave and through which the input and output laser beams would necessarily have to pass.

As briefly noted above, the CARS scattering occurs as a four-wave parametric process in which three waves, two at the pump frequency $\omega_p$ and one at the Stokes frequency $\omega_s$, are mixed in the sample to produce a coherent beam at the anti-Stokes frequency $\omega_{as}=2\omega_p-\omega_s$. The efficiency of the mixing is greatly enhanced if the frequency difference $\omega_p-\omega_s$ coincides with the frequency of a Raman-active mode of the sample. Since the Raman-active frequencies of the sample are not ordinarily known, and since it is desired to produce CARS signals from more than one mode or species, a broadband dye laser, with a bandwidth equivalent to the gain profile of the dye, is used to produce the Stokes beam. By changing the laser dye to shift the bandwidth of the Stokes beam, most Raman-active vibrational modes can be studied in a series of experiments.

Such experiments are useful for several purposes. For example, it is possible to determine changes in molecular structure and the identities of constituent species in materials, such as explosives, which undergo chemical reactions under shock-compressed conditions. Additionally, it is possible to determine basic data relating to the vibrational states of stable molecules at high pressures and high temperatures, which is useful in determining equations of state for such materials.

Figure 3:
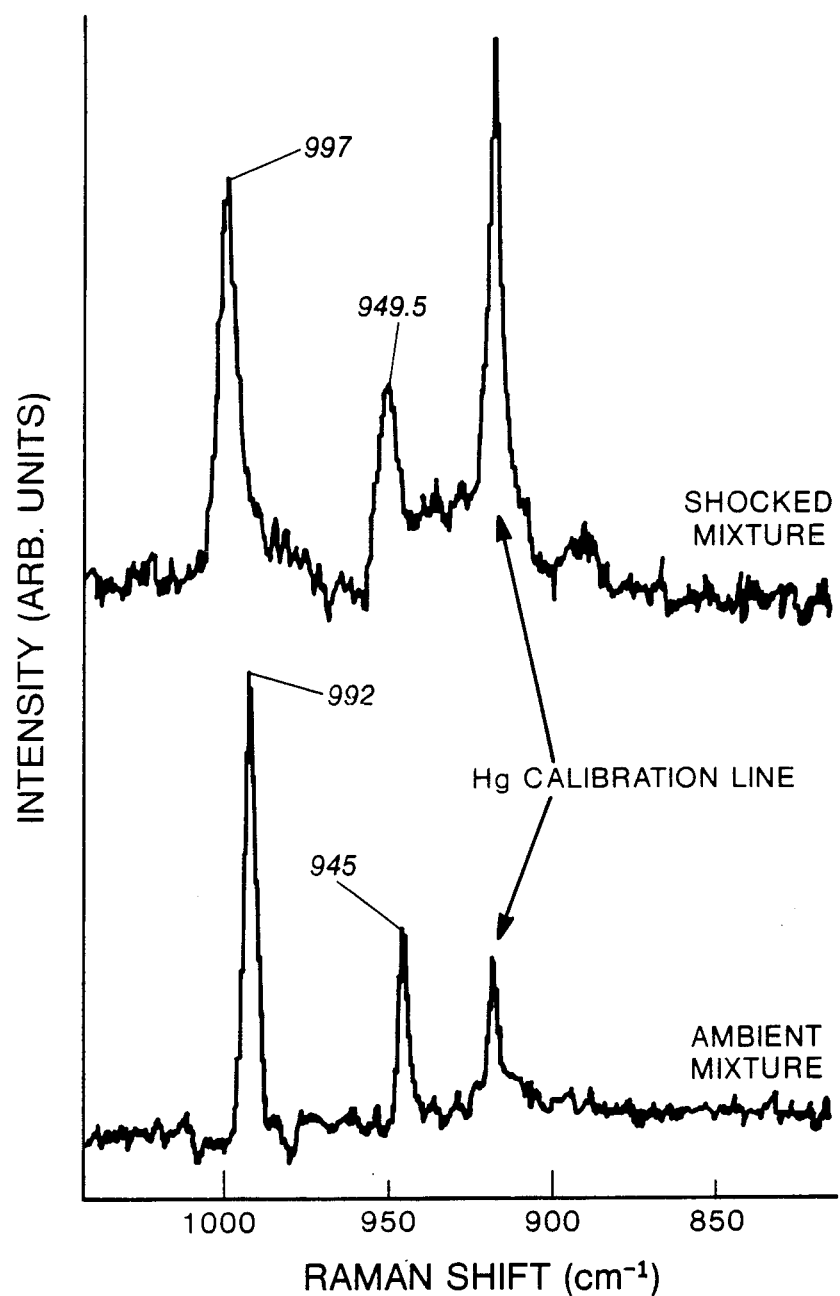
FIG. 3 presents the spectra obtained under shocked and unshocked conditions from a 60%–40% mixture of benzene and deuterated benzene, with the intensity (in arbitrary units) plotted as a function of frequency (given in reciprocal centimeters, or wave numbers).

FIG. 3 illustrates the OMA-recorded signals for the ring-stretching vibrational modes of benzene and deuterated benzene (perdeuterobenzene, or benzene-$d_6$), obtained from a sample mixture containing 60% by volume benzene and 40% benzene-$d_6$. The two plots represent the spectra obtained from the mixture under ambient (1 atmosphere) pressure conditions and under shock-compressed conditions of 0.91 GPa (9.1 kBar). As illustrated, the shock-compression of the mixture results in a shift in the benzene ring-breathing vibrational mode from 992 cm$^{-1}$ to 997 cm$^{-1}$, and a shift in the benzene-$d_6$ vibrational mode frequency from 945 to 949.5 cm$^{-1}$. Also shown is the 253.652 nm mercury reference line, which is in second order and is used as a wavelength reference. These data indicate that the ring-stretching vibrational mode for benzene has a pressure dependence of approximately 0.75 cm$^{-1}$/kBar. Among the results obtained from this demonstration, the spectral data show no evidence for the presence behind the shock wave of decomposition product species having Raman-active transitions within the vibrational frequency region spanned by the gain profile of the dye laser (i.e., between 800 and 1100 cm$^{-1}$). In addition, the spectra do not contain any evidence for deuterium exchange reactions between the deuterated and non-deuterated benzene during the 1-microsecond time period after passage of the shock wave. If deuterium exchange was occurring, new peaks would appear between the benzene and deuterated benzene transition peaks.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for conducting coherent anti-Stokes Raman scattering spectroscopy on shock-compressed materials, comprising:
    a sample containment vessel having an optically transparent window forming one wall of said vessel, and an opposing, substantially parallel optically reflective wall;
    shock means for applying a shock to said optically reflective wall so as to generate a shock wave in a sample contained in said vessel, said shock wave traveling from said reflective wall toward said optically transparent window,
    laser means for producing a pump beam and a Stokes beam, and means for directing said pump beam and said Stokes beam through said optically transparent window so as to intersect in said sample between said window and said reflective wall as said shock wave passes through said sample; and
    spectrometer means positioned to receive a coherent anti-Stokes beam emitted from the sample toward the reflective wall and reflected therefrom through the window along a path substantially parallel to the pump and Stokes beams.

2. The apparatus defined in claim 1 wherein said reflective wall is formed of polished stainless steel.

3. The apparatus defined in claim 1 wherein said laser means comprises a neodymium-yttrium aluminum garnet (Nd:YAG) laser, a portion of the output of which forms the pump beam, and a dye laser which is pumped by another portion of the output beam of the Nd:YAG laser to produce a broadband Stokes beam having frequency less than that of the pump beam.

4. The apparatus defined in claim 3 further comprising a long-wavelength-pass dichroic filter positioned in the path of the pump, Stokes and anti-Stokes beams for the purpose of separating the anti-Stokes beam from the pump and Stokes beams.

5. The apparatus defined in claim 4 wherein said spectrometer means includes a spectrometer and a silicon-intensified-target vidicon coupled to an optical multichannel analyzer.

6. The apparatus defined in claim 5 further comprising a dove prism positioned between said dichroic filter and said spectrometer for rotating the anti-Stokes beam prior to entering the spectrometer.

7. The apparatus defined in claim 1 wherein said shock means comprises a projectile fired from a high-pressure gas gun.

8. The apparatus defined in claim 1 wherein said sample containment vessel is dimensioned such that the distance between the reflective wall and the transparent window is small compared with the dimensions of the vessel in directions transverse to the direction of travel of the shock wave and the paths of the laser beams.

9. The apparatus defined in claim 8 wherein said containment vessel forms a cylindrical sample chamber.

10. A method of conducting coherent anti-Stokes Raman scattering spectroscopy on a shock-compressed material, comprising the steps of:
    containing a sample of material between an optically transparent window and an optically reflective wall; and
    applying a mechanical shock to the optically reflective wall while a pump laser beam and a Stokes laser beam are directed through the window and focused on a portion of the sample, whereby a shock wave is generated which travels through the sample from the reflective wall toward the transparent window to produce in the sample a shock-compressed zone which includes the focal point of the pump and Stokes laser beams; and
    analyzing the frequency distribution of the coherent anti-Stokes beam which is generated in the shock-compressed sample at the focal point of the pump and Stokes beams, and which is emitted toward the reflective wall and reflected therefrom back through the window along a path generally parallel to the pump and Stokes beams.

11. The method defined in claim 10 wherein the anti-Stokes beam is separated from the pump and Stokes beams by means of a long-wavelength-pass dichroic filter interposed in the path of the pump, Stokes and anti-Stokes beams.

12. The method of claim 10 wherein said pump and Stokes beams are produced by a neodymium-yttrium aluminum garnet (Nd:YAG) laser, the output of which is divided into two portions, one portion being the pump beam and the other portion being used to pump a dye laser, and with the output of the dye laser being the Stokes beam.

* * * * *